United States Patent
Maguire

(10) Patent No.: US 9,446,075 B2
(45) Date of Patent: Sep. 20, 2016

(54) COMPOSITIONS DERIVED FROM STEM CELL RELEASED MOLECULES AND METHODS FOR FORMULATION THEREOF

(71) Applicant: BioRegenerative Sciences, Inc., San Diego, CA (US)

(72) Inventor: Greg Maguire, San Diego, CA (US)

(73) Assignee: BioRegenerative Sciences, San Diego, CA (US)

( * ) Notice: Subject to any disclaimer, the term of this patent is extended or adjusted under 35 U.S.C. 154(b) by 0 days.

(21) Appl. No.: 14/218,926

(22) Filed: Mar. 18, 2014

(65) Prior Publication Data

US 2014/0205563 A1 Jul. 24, 2014

Related U.S. Application Data

(63) Continuation-in-part of application No. 13/466,132, filed on May 8, 2012, now abandoned.

(60) Provisional application No. 61/483,616, filed on May 6, 2011.

(51) Int. Cl.
*A61K 35/28* (2015.01)
*A61K 35/33* (2015.01)
*C12N 5/077* (2010.01)
*C12N 5/0775* (2010.01)
*A61K 35/12* (2015.01)
*C12N 5/071* (2010.01)

(52) U.S. Cl.
CPC .............. *A61K 35/28* (2013.01); *A61K 35/12* (2013.01); *A61K 35/33* (2013.01); *C12N 5/0628* (2013.01); *C12N 5/0656* (2013.01); *C12N 5/0667* (2013.01)

(58) Field of Classification Search
CPC .. A61K 2300/00; A61K 38/18; A61K 35/33; A61K 8/64; A61K 2800/59; A61K 45/06; A61K 35/28; C12N 2502/1382; C12N 5/0652; A61Q 7/00; A61Q 19/00; C08L 5/04; C08L 5/08
See application file for complete search history.

(56) References Cited

U.S. PATENT DOCUMENTS

| | | | |
|---|---|---|---|
| 5,091,173 A * | 2/1992 | Buultjens ................ | A61K 8/64 424/115 |
| 5,709,854 A * | 1/1998 | Griffith-Cima et al. ..... | 424/93.7 |
| 6,372,494 B1 | 4/2002 | Naughton et al. | |
| 6,692,738 B2 * | 2/2004 | MacLaughlin et al. ... | 424/93.21 |
| 7,449,333 B2 * | 11/2008 | Rolland et al. .............. | 435/325 |
| 7,459,307 B2 * | 12/2008 | Ha et al. ........ | 435/325 |
| 8,535,913 B2 * | 9/2013 | Naughton et al. ........... | 435/70.3 |
| 2008/0274185 A1* | 11/2008 | Mao .............. | 424/484 |
| 2011/0294731 A1 | 12/2011 | Torfi | |
| 2011/0300097 A1 | 12/2011 | Al-Qahtani | |
| 2012/0141410 A1 | 6/2012 | Torfi | |
| 2012/0207705 A1* | 8/2012 | Kara ................ | A61K 38/1709 424/85.2 |
| 2013/0302273 A1 | 11/2013 | Maguire et al. | |
| 2015/0071877 A1 | 3/2015 | Maguire et al. | |

FOREIGN PATENT DOCUMENTS

KR WO 2011136433 A1 * 11/2011 ............. A61K 8/981

OTHER PUBLICATIONS

Park et al., Biomedical Research 31:27-34 (2010).*
Amirjamshidi et al., "Limbal fibroblast conditioned media: A non-invasive treatment for limbal stem cell deficiency." Mol. Vis. Mar. 8, 2011 17:658-66.
Life Technologies. ADSC Catalog No. R7788-110. Feb. 13, 2009. StemPro® Human Adipose-Derived Stem Cells, 36 pages.
Oh et al., "The Anti-Inflammatory and Anti-Angiogenic Role of Mesenchymal Stem Cells in Corneal Wound Healing Following Chemical Injury." Stem Cells. Apr. 26, 2008(4)1047-55.
Polisetty et al., "Mesenchymal cells from limbal stroma of human eye." Mol Vis. Mar. 4, 2008 14:431-42.
ScienCell Research Laboratories. HDF-f Catalog No. 2300, Human Dermal Fibroblasts-fetal (HDF-f), Product Sheet retrieved Apr. 15, 2016 from http://www.sciencellonline.com/site/productInformation.php?keyword=2300, 3 pages.
ScienCell Research Laboratories. HHDPC Catalog No. 2400, Human Hair Dermal Papilla Cells (HHDPC), Product Sheet retrieved Apr. 15, 2016 from http://www.sciencellonline.com/site/productInformation.php?keyword=2400, 3 pages.
Non-Final Office Action mailed May 3, 2013 for U.S. Appl. No. 13/466,132, filed May 8, 2012.
Amendment filed Aug. 5, 2013 for U.S. Appl. No. 13/466,132, filed May 8, 2012.
Final Office Action mailed Oct. 7, 2013 for U.S. Appl. No. 13/466,132, filed May 8, 2012.
Notice of Abandonment mailed Mar. 21, 2014 for U.S. Appl. No. 13/466,132, filed May 8, 2012.
Request for Express Abandonment filed Mar. 18, 2014 for U.S. Appl. No. 13/466,132, filed May 8, 2012.
Restriction Requirement mailed Sep. 21, 2015 for U.S. Appl. No. 14/539,910, filed Nov. 12, 2014.
Amendment and Response to Restriction Requirement filed Nov. 11, 2015 for U.S. Appl. No. 14/539,910, filed Nov. 12, 2014.
Non-Final Office Action mailed Dec. 17, 2015 for U.S. Appl. No. 14/539,910, filed Nov. 12, 2014.

(Continued)

*Primary Examiner* — Daniel C Gamett
(74) *Attorney, Agent, or Firm* — Knobbe Martens Olson & Bear LLP

(57) ABSTRACT

Compositions for use in treatment of a variety of tissue diseases include stem cells and stem cell released molecules (SRM's) suspended in an aqueous solution with a cellulosic material or other thickening agent. The stem cells and SRM's can be derived from one or more distinct cell lines. The SRM's can further include one or more mucins, cytokines, or growth factors. Exemplary formulations include stem cells and SRMs derived from epithelial stem cells, corneal limbal stem cells, and fibroblasts. Other compositions and methods for formulation thereof are described.

14 Claims, 1 Drawing Sheet

(56) References Cited

OTHER PUBLICATIONS

Brigham, Pamela A et al., (1988), "The Stumptailed macaque as a Model for Andro-genetic Alopecia: Effects of Topical Minoxidil Analyzed by Use of the Folliculogram", Clin. Dermatol., 6(4):177-187.
Diani AR et al., (1994), "Immunocytochemical Localization of Androgen Receptors in the Scalp of Stumptail Macaque Monkey, a Model of Androgenetic Alopecia", Invest. Dermatol., 102(4):511-514.
Doyle et al., *Cell & Tissue Culture: Laboratory Procedures in Biotechnology*, John Wiley & Sons Ltd., 1998, Chichester, England.
Flax et al., (1998), "Engraftable human neural stem cells respond to developmental cures, replace neurons, and express foreign genes", Nature Biotechnol., 16(11):1033-1039.
Frisen et al., (1998), "Central nervous system stem cells in the embryo and adult", Cell. Mol. Life Sci., 54:935-945.
Holland, J Michael et al., (1988), "Animal Models of Alopecia", Clin. Dermatol., 6(4):159-162.
Hussein Atif M., (1995), "Protection Against Cytosine Arabinoside-Induced Alopecia by Minoxidil in a Rat Animal Model", Int. J. Dermatil., 34(7):470-473.
Keller et al., (1999), "Human embryonic stem cells: The future is now", Nature Med., 5(2):151-152.
Kuno et al., (2011), "Recent Advances in Ocular Drug Delivery Systems", Polymers, 3:193-221.
Liss, Alan R., *Culture of Animal Cells: A Manual of Basic Technique*, 2$^{nd}$ Edition, Edited by R. Ian Freshney, Table of Contents, 1987, New York.
Liss, Alan R., *Methods for Preparation of Media, Supplements and Substrate for Serum-Free Animal Cell Culture*, Table of Contents, New York, 1984.
MacKay et al., (1998), "Chondrogenic Differentiation of Cultured Human Mesenchymal Stem Cells from Marrow", Tissue Eng., 4:415-428.
McElwee KJ et al., (1990), "Immunobiological studies on the alopecic (DEBR) rat", Br. J. Dermatol., 123(5):557-567.
Neste DV, (1996), "The Growth of Human Hair in Nude Mice", Dermatol. Clin., 14(4):609-617.
Oliver RF et al., (1991), "The DEBR Rat Model of Alopecia Areata", J. Invest. Dermatol., 96(5):978.
Pan HJ et al., (1998), "Evaluation of RU58841 as an Anti-Androgen in Prostate PC3 Cells and a Topical Anti-Alopecia Agent in the Bald Scalp of Stumptailed Macaques", Endocrine, 9(1):39-43.
Rittmaster RS et al., (1987), "The Effects of $N,N$-Diethyl-4-Methyl-3-Oxo-4-Aza-5α-Androstane-17β-Carboxamide, a 5α-Reductase inhibitor and Antiandrogen, on the Development of Baldness in the Stumptail Macaque*", J. Clin. Endocrinol. Metab., 65(1):188-93.
Shamblott et al., (1998), "Derivation of pluripotent stem cells from cultured human primordial germ cells", PNAS, 95:13726-1371.
Smith, (1998), "Cell therapy: In search of pluripotency", Curr. Biol., 8:R802-804.
Thomson et al., (1998), "Embryonic Stem Cell Lines Derived from Human Blastocysts", Science, 282:1145-1147.
Williams et al., (1999), "Cells Isolated from Adult Human Skeletal Muscle Capable of Differentiating into Multiple Mesodermal Phenotypes", Am. Surg., 65:22-26.
Amendment filed Apr. 18, 2016 for U.S. Appl. No. 14/539,910, filed Nov. 12, 2014.

* cited by examiner

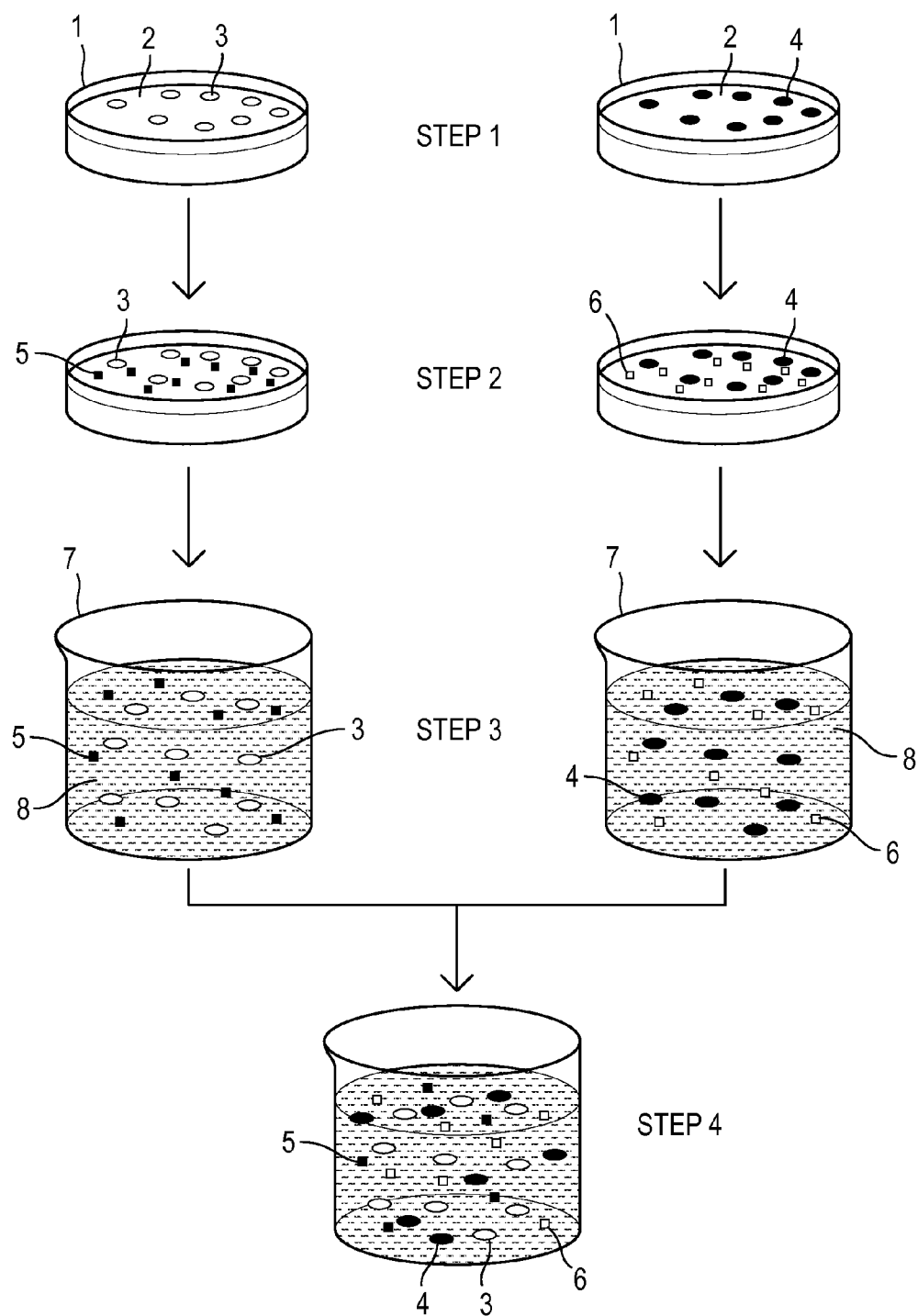

COMPOSITIONS DERIVED FROM STEM CELL RELEASED MOLECULES AND METHODS FOR FORMULATION THEREOF

CROSS-REFERENCE TO RELATED APPLICATIONS

This application is a continuation in part (CIP) of U.S. Ser. No. 13/466,132, filed May 8, 2012; which claims benefit of priority to U.S. Provisional Ser. No. 61/483,616, filed May 6, 2011; the contents of each of which are hereby incorporated by reference.

BACKGROUND OF THE INVENTION

1. Field of the Invention

This invention relates generally to compositions for tissue repair and methods for formulation thereof; and more particularly to compositions containing a therapeutic amount of stem cell released molecules for stimulating cytogenesis, cytoprotection, immune modulation, and pain relief in a targeted tissue region, such as opthalmic tissue, and the like.

2. Description of the Prior Art

It is widely known that stem cells are capable of producing and secreting certain molecules collectively referred to herein as "stem cell released molecules" (SRM), including for example: growth factors, cytokines, anti-oxidants, micro-RNA, mucins, and other molecules. A number of experimental therapies have emerged in the art that incorporate one or more stem cells for the treatment of a myriad of health related diseases and disorders.

Although various treatments have been investigated, these treatments have focused on providing live stem cells. Certain disadvantages related to treatment compositions consisting of live stem cells includes uncertainty of whether the provided cells are indeed alive at the time of delivery to the target tissue, whether the cells reach the target tissue, and whether the provided cells are capable of producing and releasing SRM's for facilitating a repair response in vivo.

As technologies advance and stem cell lines and other requisites become available, there is a continued need to develop formulations for treatment of tissue related diseases and associated symptoms.

By way of example, a common ophthalmic condition known as "dry eye" or "ocular surface disease" is generally understood to be caused by a problem with the quality of the tear film that lubricates the eyes. However, the tear film has long been thought to comprise three or more layers, of which a middle layer of the tear film has long been thought to include water for moisturizing the eyes. More recently, research has shown that the tear film of those with ocular surface disease generally lacks sufficient mucins and other naturally occurring molecules that would be present in a healthy patient. Thus, modern research confirms that a primary cause of ocular surface disease is generally a lack of mucins and other molecules for cellular repair and proliferation within the tear film as opposed to a reduction in the moisture content of the tear film itself. Accordingly, there has been much research in the field for seeking improved treatments for ocular surface disease, or dry eye.

Other ocular surface diseases include conjunctivitis, corneal erosion, keratitis, and corneal ulcers.

In the prior art, treatments for dry eye focused on providing moisture to the eye, and thus included various saline solutions, and other moisturizing solutions. One problem with these solutions includes that repeated use of such solutions can flush important proteins and other molecules from the eye. Without these naturally occurring molecules, the eyes are restricted from healing, and thus what is a temporary relief of pain and discomfort by providing a moisturizing solution to the eye, in fact may be a cause of further damage by flushing out important molecules. Thus, a limitation includes that prior art compositions fail to restore important biological molecules to the eye where such molecules would be beneficial to the healing process.

Although ocular surface disease, and ophthalmic compositions are described herein, this invention is not limited to these applications and compositions. Instead, the above details are provided as an example of certain limitations in the art. The invention will be further described hereinafter, and the scope of the invention should not be construed as limited by the above examples as those having skill in the art would recognize the features and benefits herein as applied to various alternative indications.

BRIEF SUMMARY OF THE INVENTION

This invention discloses unique compositions for the treatment of certain diseases, and in a general embodiment a composition comprises: a therapeutic amount of stem cell released molecules (SRM's) including at least one of: growth factors, cytokines, anti-oxidants, micro-RNA, and mucins; and a carrier for suspending said stem cell released molecules in a solution for delivery, the carrier adapted for topical, oral, injectable, or other forms of delivery of the SRM's to a targeted delivery site, wherein said composition is adapted to stimulate cytogenesis, cytoprotection, immune modulation, and pain relief within tissue adjacent to the targeted delivery site.

In one embodiment of the invention, an opthalmic composition is provided for treatment of keratoconjunctivitis sicca (KCS) otherwise referred to as "dry eye", the composition comprises an amount of stem cells and SRM's derived from a first cell line, and amount of stem cells and SRM's derived from a second cell line. The stem cells and SRM's of the first cell line are collectively referred to as a first adjuvant material while those of the second cell line are referred to as a second adjuvant material. Each of the first and second cell lines individually comprises one of: mesenchymal stem cells, epithelial stem cells, limbal stem cells, other stem cell types, or fibroblasts, wherein the first and second cell lines are distinct with respect to each other. The composition further comprises a thickening agent, the thickening agent comprising at least one of: a cellulosic material, or a polymer. The first adjuvant material, second adjuvant material, and thickening agent are further combined in an aqueous solution to form a therapeutic ophthalmic composition for the treatment of KCS. The composition can additionally comprise one or more electrolytes, vitamin A, or preservatives.

In various embodiments, the compositions disclosed herein are adapted to protect an ocular surface from dryness, absorb shear forces of the blink, as well as assist gel forming mucins in maintaining their viscoelastic properties and ensuring structure and stability of the tear film.

In other embodiments of the invention, a therapeutic composition includes a first adjuvant material comprising at least one of: stem cells and stem cell released molecules, the stem cells and SRM's of the first adjuvant material each being derived from a first stem cell line; a second adjuvant material comprising at least one of: stem cells and stem cell released molecules, the stem cells and SRM's of the second adjuvant material each being derived from a second stem cell line; and a thickening agent. In each of these embodiments, the first stem cell line is distinct from the second stem cell line for promoting an emergent healing response in vivo.

In another aspect of the invention, certain methods are disclosed for formulation of these compositions, a general method comprising: providing an amount of first stem cells; culturing the first stem cells in vitro such that the first stem cells are stimulated to secrete one or more SRM's; introducing a thickening agent; and suspending the first stem cells, SRM's, and thickening agent in an aqueous solution.

In certain embodiments, a method for formulation of a therapeutic composition further includes the steps of: providing an amount of second stem cells, the second stem cells being distinct from the first stem cells; culturing the second stem cells in vitro such that the second stem cells are stimulated to secrete one or more SRM's; and combining the first and second stem cells and SRM's.

Other embodiments will become apparent upon a thorough review of the following detailed description of the preferred embodiments.

BRIEF DESCRIPTION OF THE DRAWINGS

These and other attributes of the invention are further described in the following detailed description, particularly when reviewed in conjunction with the drawings, wherein:

FIG. 1 illustrates a schematic flow chart representing a general embodiment of the invention, wherein an amount of stem cells and SRM's derived from a first cell line are combined with an amount of stem cells and SRM's derived from a second stem cell line to form a therapeutic composition.

DETAILED DESCRIPTION

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention. Certain embodiments will be described below with reference to the drawings wherein illustrative features are denoted by reference numerals.

To assist those having skill in the art with making and using the invention, the following terms being particularly relevant to one or more embodiments herein are hereby defined as follows:

the term "mesenchymal stem cell" is herein defined as any multi-potent stem cell capable of differentiation into a variety of cell types;

the term "epithelium" is herein defined as membranous tissue composed of one or more layers of cells separated by very little intercellular substance and forming the covering of most internal and external surfaces of the body and its organs comprising one or more epithelial cell types;

the term "epithelial stem cell" is herein defined as a stem cell being capable of differentiation into a variety of epithelial cell types;

the term "limbus" is herein defined as a distinctive border or edge, such as the junction between the cornea and sclera of the eyeball comprising one or more limbal cell types;

the term "limbal stem cell" is herein defined as a stem cell capable of differentiation into a variety of limbal cell types;

the term "fibroblast" is herein defined as a cell that gives rise to connective tissue;

the term "mucin" is herein defined as any of a group of protein-containing glycoconjugates with high sialic acid or sulfated polysaccharide content that compose the chief constituent of mucus;

the term "cytokine" is herein defined as a generic term for nonantibody proteins released by one cell population on contact with specific antigen, which act as intercellular mediators, as in the generation of an immune response;

the term "growth factor" is herein defined as a chemical made by cells that acts on other cells to stimulate or inhibit their function;

the term "interleukin" is herein used as a generic term for a group of multifunctional cytokines that are produced by a variety of lymphoid and nonlymphoid cells and whose effects occur at least partly within the lymphopoietic system;

the term "adjuvant" is herein defined as a nonspecific stimulator of an immune response;

the term "cellulosic material" is herein defined as a derivative of cellulose;

the term "stem cell released molecules" or SRM's is a generic term for a group of chemicals, proteins, and other molecules produced or secreted by stem cells and comprises mucins, cytokines, and growth factors; and the term "cell line" is herein defined as any laboratory-isolated cell type.

Now, with reference to the invention and various embodiments herein, a therapeutic composition generally comprises an amount of stem cells and stem cell released molecules (SRM's) being derived from a first cell line by in vitro culture. The stem cells and SRM's are generally cultured in a nutrient medium by way of Petri dishes, flasks, and the like. Once sufficient SRM's are produced, the cells and SRM's are suspended in an aqueous solution. A thickening agent, such as a cellulosic material or polymer may be provided for enhancing viscosity of the composition. In this regard, a therapeutic composition can be administered to a patient for moisturizing a tissue region and delivering important bioactive materials such as SRM's for stimulating a healing response in damaged tissue.

In certain embodiments, the composition further includes an amount of stem cells and SRM's derived from a second cell line, wherein the second cell line is distinct from the first cell line. In this regard, a plurality of stem cells and SRM's can be administered to effectuate a synergistic and emergent healing response in vivo.

In one embodiment, three or more cell lines are provided and cultured to yield respective SRM's, wherein each of the cell lines is distinct from each other.

Many cell lines are commercially available in the art, however each indication should be appropriately matched with one or more targeted cell lines. For example, in an effort to treat keratoconjunctivitis sicca (KCS), otherwise referred to as "dry eye", or "ocular surface disease", a therapeutic composition can include those cells and SRM's which may naturally occur in the tissues relating to and surrounding the eyes, such as the ophthalmic tissues including the cornea, conjunctiva, and other eye tissues. In the case of KCS, a patient requires a healing response in the ophthalmic tissues, and more specifically the tear film adjacent to the cornealscleral tissues, and thus a therapeutic composition can be tailored accordingly.

By way of example, in one embodiment of the invention a therapeutic composition is provided for the treatment of KCS, the composition comprises: an amount of stem cells and SRM's derived from a first cell line, and an amount of stem cells and SRM's derived from a second cell line. The stem cells and SRM's of the first cell line are collectively referred to as a first adjuvant material, while those of the second cell line are referred to as a second adjuvant material. Each of the first and second cell lines individually comprises one of: mesenchymal stem cells, epithelial stem cells, limbal stem cells, or fibroblasts, wherein the first and second cell lines are distinct with respect to each other. The composition further comprises a thickening agent, the thickening agent comprising at least one of: a cellulosic material, or a polymer. The first adjuvant material, second adjuvant material, and thickening agent are further combined in an aqueous solution to form a therapeutic ophthalmic composition for the treatment of KCS. The composition can additionally comprise one or more electrolytes, vitamin A, or preservatives.

In this regard, certain mesenchymal stem cells, epithelial stem cells, limbal stem cells, and fibroblasts tend to naturally occur within human eye tissues. Each of these types of cells is therefore capable of producing one or more SRM's useful in maintaining the integrity and health of the human eye tissue. SRM's may include for example: mucins, cytokines, and growth factors for stimulating a cytogenesis, immune modulation, or repair response in the targeted tissue.

Mucins are a family of high molecular weight, heavily glycosylated proteins (glycoconjugates) produced by epithelial tissues. Mucins' key characteristic is their ability to form gels; therefore they are a key component in most gel-like secretions, serving functions including lubrication, cell signaling, and forming chemical barriers, among others.

Ocular surface mucins are highly glycosylated proteins which provide structure the tear film by binding both to each other and to the aqueous component of the tear film, helping to stabilize the tear film. Mucins are essential for maintaining ocular surface health. In a healthy eye, the concentration of ocular surface mucins is highest near the surface of the globe, and it gradually decreases as the tear/air interface is approached.

Within this gradient, different types of mucins are believed to occupy different positions and perform different functions. For example, secreted mucins, such as MUC4 and MUC7, are produced by the lacrimal gland. These are the smallest mucin molecules in the tear film. Additionally, gel-forming mucins, such as MUC5-AC, are secreted by the goblet cells of the conjunctiva. Like the secreted mucins, gel-forming mucins are dissolved in the tear film, but gel-forming mucins are larger and more interactive with other mucin molecules. Furthermore, membrane-associated mucins, such as MUC1 and MUC16, are even longer molecules that have an intracellular extension serving to anchor them to epithelial cells. These mucins play a key role in protecting the ocular surface, and when these mucins are absent or damaged ocular surface staining results. Other mucins in the tear film include MUC2, among others.

These and other mucins have been produced by in vitro culture of limbal stem cells, and have been further incorporated into various compositions in accordance with embodiments of the invention.

Cytokines include immunomodulating agents, such as interleukins and interferons. These agents are capable of soliciting and inducing an immune response in vivo.

In the tear film of the eye, a higher concentration of cytokines, such as interleukin (IL)-2, IL-4, IL-5, IL-6, IL-10, interferon (IFN)-gamma, tumor necrosis factor (TNF)-alpha, and IL-1 beta, has been shown to correlate with severity of dry eye syndrome. It is believed that these cytokines are responsible for promoting a healing response in patients with ocular surface disease. Accordingly, these and other related cytokines have been incorporated into various compositions in accordance with certain embodiments of the invention. Generally, the cytokines are secreted by limbal stem cells in vitro using a culturing technique. Once produced, the cytokines are suspended in a solution and delivered to the targeted tissue in accordance with various embodiments herein.

Growth factors are naturally occurring substance capable of stimulating cellular growth, proliferation and cellular differentiation. Growth factors generally include proteins and steroid hormones, and are important for regulating a variety of cellular processes.

Numerous biologically active growth factors are secreted by the lacrimal gland and distributed via the tears over the ocular surface, where they affect cellular proliferation, migration, differentiation, and survival. Epidermal growth factor release rates have been shown to be significantly lower in eyes with ocular surface diseases than in normal eyes during reflex tearing.

Examples of growth factors include: LIF, VEGF, HGF, SDF, SCF, M-CSF, bFGF, IGFBP, Oncostatin M, MIP1-beta, TIMP-2, TGFbeta-1, TGFbeta-2, PDGF, EGF, KGF, GM-CSF, HGF, MCP-1, TNFalpha, FGF-2, Flt-3, PDGF-AA, and TGF-beta3.

Keratinocyte growth factor (KGF) and hepatocyte growth factor (HGF), among others, have been obtained by in vitro culture of stem cells and incorporated into therapeutic compositions according to various embodiments of the invention.

In various embodiments, stem cells are generally stimulated to induce secretion of targeted SRM's in culture. This is generally accomplished by introducing the cultured cells to certain antigens, cytokines, and other molecules during in vitro processing to simulate a bio-condition. In this regard, certain antigens or other stimulants may stimulate the cultured cells into producing the targeted SRM's. Furthermore, the cells can further differentiate into specific cell types, or matured in vitro by introducing certain antigens, proteins, and other bio-molecules. Throughout the culturing process, the stem cells can be transformed into differentiated or matured cells, and SRM's can be synthesized through one or more simulated bio-conditions in vitro. Thus, the harvested cells can be transformed and new molecules produced through in vitro culturing.

In certain embodiments, cells are manipulated in culture by any of: depleting a culture medium of certain nutrients to replicate a bio-condition; accumulating dead or ablated cells in the nutrient medium; and cell to cell contact to stimulate differentiation and maturation of cells, or other technique known to those having skill in the art.

In certain embodiments, a thickening agent can be incorporated into the composition for increasing viscosity thereof. The thickening agent can be any cellulosic material, such as methyl cellulose, sodium carboxymethyl cellulose, and hydroxypropylmethyl cellulose. Alternatively, certain polymers can be incorporated as thickening agents, such as carboxyvinyl polymer, polyvinyl alcohol, polyvinyl pyrrolidone, polyethylene glycol, and polysorbate 80.

Although certain ophthalmic compositions are described herein, the invention can be applied to a wide variety of tissue conditions, such as: colonitis, diabetic ulcers, among others. Furthermore, although several embodiments provide a composition for topical administration, such as eye drops, gels, and creams, it is within the scope of the invention to provide injectable compositions and the like.

In another aspect of the invention, certain methods are disclosed for formulation of these compositions, a general method comprising: providing an amount of first stem cells;

culturing the first stem cells in vitro such that the first stem cells are stimulated to secrete one or more SRM's; introducing a thickening agent; and suspending the first stem cells, SRM's, and thickening agent in an aqueous solution.

In certain embodiments, a method for formulation of a therapeutic composition further includes the steps of: providing an amount of second stem cells, the second stem cells being distinct from the first stem cells; culturing the second stem cells in vitro such that the second stem cells are stimulated to secrete one or more SRM's; and combining the first and second stem cells and SRM's in a suspension.

Now turning to a representative schematic, FIG. 1 illustrates a general method according to the invention, the method including the steps of: (Step 1) providing cells in a Petri Dish 1, flask, or other object, the cells comprising a first cell line 3 in a first flask and a second cell line 4 in a second flask, keeping the first and second cell lines separate. Each of the cells of the first and second cell lines are suspended in a nutrient medium 2 as understood by those having skill in the art; (Step 2) culturing the cells from the first and second cell lines in vitro for producing one or more SRM's 5; 6 from each cell line; (Step 3) suspending the stem cells and SRM's of each cell line in an aqueous solution 8; and (Step 4) combining the cells and SRM's from the two cell lines to formulate a therapeutic composition comprising an amount of first stem cells 3, an amount of second stem cells 4, an amount of first SRM's 5, and amount of second SRM's 6, and an aqueous solution 8.

One or more preservatives or other materials can be provided to the mixture for enhancing the therapeutic or other properties of the composition.

EXAMPLE 1

50/50 Composition of ADSC and HDF-f Derived SRM's in an Aqueous Suspension

In one example, a therapeutic composition for treatment of ocular surface disease includes about 50% SRM's derived from Human Adipose Derived Stem Cells (ADSC) and about 50% SRM's derived from Human Dermal Fibroblasts (HDF-f) by volume.

In accordance with embodiments of the invention, an amount of ADSC and an amount of HDF-f cell lines were individually provided in nutrient media and thawed in a water bath prior to sub culturing (passaging) in flasks. Upon reaching about 90% confluence, the respective SRM's were harvested. Here, a sterile pipette was used to remove medium containing the ADSC and SRM's from flasks and transferred to a 500 mL filter unit having a 0.33 uM pore size. Upon transfer of the medium, vacuum was applied and the SRM's were filtered into a receptacle. The SRM's were then aliquoted and stored in sterile containers for subsequent use.

Subsequent to removing SRM's from the ADSC medium, the cells were passaged and frozen. Dulbecco's phosphate buffered saline (DPBS) was used to lift cells from the surface of flasks and Mesenpro RS medium was used for culture.

The HDF-f cells were similarly processed to extract SRM's, passage cells, and freeze. HDF-f cells were cultured in fibroblast medium.

The ADSC SRM's and HDF-f SRM's were thawed in a water bath at 37° C. and combined in a 50/50 ratio by volume. The SRM's were filtered by vacuum into an all-in-one receptacle and stored in a sterile container at 4° C.

EXAMPLE 2

Composition for Hair Growth Treatment

In another example, a hair growth treatment product is produced in accordance with the above methods. In this example, a technician obtains a source of first stem cells, for example StemPro® Human Adipose-Derived Stem, catalogue code R7788115 from Life Technologies (www.lifetechnologies.com), and a source of second stem cells, for example HUMAN HAIR DERMAL PAPILLA CELLS (HHDPC): Catalog #2400 from ScienCell Research Laboratories (http://www.sciencellonline.com), and a third source of stem cells, for example Human Dermal Fibroblasts-fetal (HDF-f), Catalog #2300 from ScienCell Research laboratories.

In accordance with embodiments of the invention, an amount of ADSC, HHDPC, and an amount of HDF-f cell lines were individually provided in nutrient media and thawed in a water bath prior to sub culturing (passaging) in flasks. Upon reaching about 90% confluence, the respective SRM's were harvested. Here, a sterile pipette was used to remove medium containing the ADSC and SRM's from flasks and transferred to a 500 mL filter unit having a 0.33 uM pore size. Upon transfer of the medium, vacuum was applied and the SRM's were filtered into a receptacle. The SRM's were then aliquoted and stored in sterile containers for subsequent use.

Subsequent to removing SRM's from the ADSC medium, the cells were passaged and frozen. Dulbecco's phosphate buffered saline (DPBS) was used to lift cells from the surface of flasks and Mesenpro RS medium (Catalogue #12746012, LifeTechnologies) was used for culture.

The HDF-f cells and HHDPC cells were similarly processed to extract SRM's, passage cells, and freeze. HDF-f cells were cultured in fibroblast medium Fibroblast Medium (FM, Cat. No. 2301, ScienCell Res. Labs) and HHDPC cells were cultured in Mesenchymal Stem Cell Medium (MSCM, Cat. No. 7501, ScienCell Res. Labs)

The ADSC SRM, HHDPC SRM, and HDF-f SRM were thawed in a water bath at 37° C. and combined in a 33/33/33 ratio by volume. The SRM's were filtered by vacuum into an all-in-one receptacle and stored in a sterile container at 4° C.

In accordance with the embodiment above, fibroblasts have been shown to release a SRM that includes the following molecules: Osteonectin, decorin, collagens I,III,IV, V, fibronectin, fibrillin, laminins, and hyaluronic acid. Each of these molecules can be harvested and incorporated into the composition for hair growth treatment.

In accordance with the embodiment above, mesenchymal stem cells have been shown to release molecules that include: HLA-A, -B, and -C, exosomes, MSC IL-6, M-CSF, PGE2, IDO, TGF-, HLA-G, and PGE2, IL-1, IL-6, GDNF, BDNF, IGF-1, VEGF, GDNF, NGF, bFGF, BMP-4, bFGF, VEGF, PDGF, IL-1β, IL-10, stem cell-derived factor-(SDF-) 1, HGF, IGF-1, thymosin-β4, and Wnt5a, IL-113 and TNF-a, bFGF, HGF, angiopoietin-1 and -2 (Ang-1 and -2), cysteine-rich protein 61, antioxidants, proteasomes. Each of these molecules can be harvested and incorporated into the composition for hair growth treatment.

In accordance with the embodiment above, HUMAN HAIR DERMAL PAPILLA CELLS (hHDP) have been shown to release molecules that include: Wnt and Bmp, SOX2, beta-catenin. The (hHDP) cells must be cultured only through early passage because in the state of early passage the hHDP produce only positive hair growth factors, whereas in later passages, the state of the hHDP produces and releases molecules, such as interferon beta, that are negative regulators of hair growth. Each of these molecules can be harvested and incorporated into the composition for hair growth treatment.

While particular embodiments of the present invention have been disclosed, it is to be understood that various modifications and combinations are possible and are contemplated within the true spirit and scope of the appended claims. There is no intention, therefore, of limitations to the exact abstract and disclosure herein presented.

The invention claimed is:

1. A method for forming a therapeutic composition, comprising:
    culturing cells of a first cell line and a second cell line in a first and a second respective culture medium, wherein said cells secrete extracellular products into the respective culture medium so that a first conditioned medium and a second conditioned medium are respectively formed;
    harvesting said first and second conditioned medium by removing cultured cells from said respective conditioned medium; and
    combining said first conditioned medium and second conditioned medium to form a therapeutic composition,
    wherein said first and second cell lines are an adult human adipose-derived stem cell line (ADSC), and a fetal human fibroblast cell line.

2. The method of claim 1, wherein said first cell line is a StemPro® human adipose-derived stem cell line (ADSC) provided by Life Technologies Catalog Number R7788115.

3. The method of claim 1, wherein said second cell line is a fetal human dermal fibroblast (HDF-f) cell line provided by ScienCell Research Laboratories Catalog Number 2300.

4. The method of claim 1, wherein said first conditioned medium and said second conditioned medium are combined in a ratio of about 50/50 by volume.

5. The method of claim 1, further comprising
    culturing cells of a third cell line in a third culture medium, wherein said cells of said third cell line are different from those of the first and second cell lines and they secrete extracellular products into said third culture medium so that a third conditioned medium is formed; and
    incorporating said third conditioned medium into said therapeutic composition,
    wherein said third cell line is a human hair dermal papilla cell line (HHDPC).

6. The method of claim 5, wherein cells of said human hair dermal papilla cell line (HHDPC) are cultured only through early passage.

7. The method of claim 5, wherein said first, second, and third conditioned media are combined in a ratio of about 33/33/33 by volume.

8. The method of claim 1, further comprising incorporating a thickening agent into each of said conditioned media prior to the combining step.

9. The method of claim 8, wherein said thickening agent comprises one or more cellulosic material or polymer.

10. The method of claim 9, wherein said thickening agent comprises one or more cellulosic material selected from the group consisting of methyl cellulose, sodium carboxymethyl cellulose, and hydroxypropylmethyl cellulose.

11. The method of claim 9, wherein said thickening agent comprises one or more polymer selected from the group consisting of carboxyvinyl polymer, polyvinyl alcohol, polyvinyl pyrolidone, polyethylene glycol, and polysorbate 80.

12. The method of claim 1, wherein said first cell line is a StemPro® human adipose-derived stem cell line (ADSC) provided by Life Technologies Catalog Number R87788115, and the second cell line is a fetal human dermal fibroblast (HDF-f) cell line provided by ScienCell Research Laboratories Catalog Number 2300.

13. A therapeutic composition formed by a method according to claim 1.

14. The therapeutic composition of claim 13, wherein said therapeutic composition is formulated for topical administration.

* * * * *

UNITED STATES PATENT AND TRADEMARK OFFICE
CERTIFICATE OF CORRECTION

PATENT NO. : 9,446,075 B2
APPLICATION NO. : 14/218926
DATED : September 20, 2016
INVENTOR(S) : Greg Maguire and Peter Friedman Page 1 of 1

It is certified that error appears in the above-identified patent and that said Letters Patent is hereby corrected as shown below:

On the Title Page

Item (75), Inventors, After "Greg Maguire, San Diego, CA (US)" insert --Peter Friedman, Ocala, FL (US)--.

Signed and Sealed this
Ninth Day of October, 2018

Andrei Iancu
*Director of the United States Patent and Trademark Office*